United States Patent [19]
Langhals et al.

[11] Patent Number: 6,166,210
[45] Date of Patent: Dec. 26, 2000

[54] PERYLENE IMIDE MONOCARBOXYLIC ACIDS

[75] Inventors: Heinz Langhals, Ottobrunn; Wolfgang Jona, Waldkraiburg, both of Germany

[73] Assignee: Ciba Specialty Chemicals Corporation, Tarrytown, N.Y.

[21] Appl. No.: 09/204,189

[22] Filed: Dec. 3, 1998

[30] Foreign Application Priority Data

Dec. 15, 1997 [EP] European Pat. Off. .............. 97810981

[51] Int. Cl.⁷ ................................. C07D 221/18
[52] U.S. Cl. ................................................ 546/37
[58] Field of Search ........................ 546/36, 37

[56] References Cited

U.S. PATENT DOCUMENTS

| | | | |
|---|---|---|---|
| 4,594,420 | 6/1986 | Spietschka et al. | 546/29 |
| 4,599,408 | 7/1986 | Spietschka et al. | 544/125 |
| 4,709,029 | 11/1987 | Spietschka et al. | 544/125 |
| 4,978,755 | 12/1990 | Babler et al. | 546/37 |
| 5,248,774 | 9/1993 | Dietz et al. | 544/125 |
| 5,264,034 | 11/1993 | Dietz et al. | 106/493 |

FOREIGN PATENT DOCUMENTS

| | | |
|---|---|---|
| 039 482 | 11/1981 | European Pat. Off. . |
| 039085 | 11/1981 | European Pat. Off. . |
| 122442 | 10/1984 | European Pat. Off. . |
| 283 436 | 9/1988 | European Pat. Off. . |
| 504 872 | 9/1992 | European Pat. Off. . |
| 1570579 | 6/1969 | France . |
| 3926564 | 2/1991 | Germany . |
| 4338784 | 5/1995 | Germany . |
| 96/223 332 | 7/1996 | WIPO . |

OTHER PUBLICATIONS

J. Phys. Chem. B 101 (1997) pp. 4490–4493.
Liebigs Ann. (1995) pp. 1229 f.
Liebigs Ann./Receuil (1997) pp. 467 f.
Patent abstracts of Japan vol. 104, No. 475 for JP 01 196 885, 1990.
Abstract of EP 0 039 085, 1981.
Derw. Abst. 96–354498 [35] of WO 96/22332, 1996.
Derw. Abst. 95–186680 [25] of DE 4,338,784, 1995.
Derw. Abst. 68–362248Q [00] of FR 1,570,579, 1969.
Menikh et al., Chem. Abstract: 110:77509, 1997.
Akira et al., Chem. Abstract: 129: 97756, 1998.
Windser et al., Chem. Abstract: 127: 4792, 1997.
Mishra et al. Chem. Abst. 127: 163030 (1997).
Menikh et al. Chem. Abst. 127: 4792 (1997).

*Primary Examiner*—Richard L. Raymond
*Attorney, Agent, or Firm*—David R. Crichton

[57] ABSTRACT

Perylene imide monocarboxylic acids of the general formula I

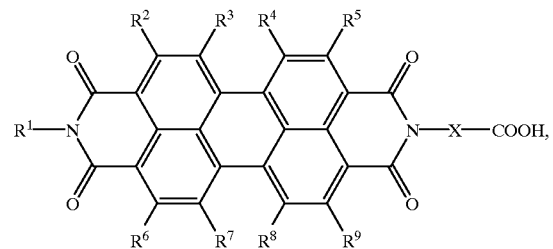

perylene-3,4-dicarboxylic acid imides, perylene imide carboxylic acid derivatives and a process for the preparation of these compounds as well as their use, inter alia, as colourants.

3 Claims, No Drawings

PERYLENE IMIDE MONOCARBOXYLIC ACIDS

The present invention relates to perylene imide monocarboxylic acids of the general formula

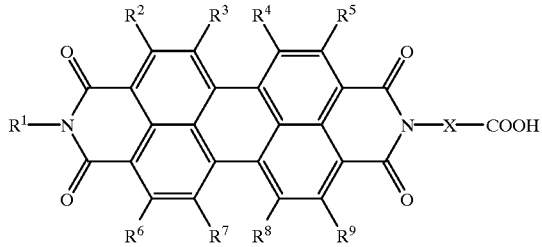

(I)

wherein $R^1, R^2, R^3, R^4, R^5, R^6, R^7, R^8, R^9$ are identical or different and are hydrogen, or one to nine radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{10}$, —CN, —$NR^{11}R^{12}$, —$COR^{13}$, —$NR^{14}COR^{13}$, —$NR^{10}COOR^{13}$, —$NR^{10}CONR^{11}R^{12}$, —$NHSO_2R^{13}$, —$SO_2R^{13}$, —$SOR^{13}$, —$SO_2OR^{13}$, —$CONR^{11}R^{12}$, —$SO_2NR^{11}R^{12}$, —$N=NR^{15}$, —$OCOR^{13}$ and —$OCONHR^{13}$, wherein pairs of adjacent radicals can form a carbocyclic or heterocyclic ring, wherein $R^{13}$ is $C_1$–$C_{18}$alkyl, $C_6$–$C_{10}$aryl, or benzyl which is unsubstituted or substituted by halogen, $C_1$–$C_4$alkyl or $C_1$–$C_4$alkoxy, or a five- to seven-membered heterocyclic radical, $R^{11}$ and $R^{12}$ are each independently of the other hydrogen; $C_1$–$C_{18}$alkyl, $C_3$- to $C_{24}$cycloalkyl, $C_6$–$C_{10}$aryl or 5- to 7-membered heteroaryl, each of which is unsubstituted or substituted by cyano groups or hydroxy groups, or wherein $R^{11}$ and $R^{12}$, together with at least one of the other radicals $R^2$ to $R^9$, are a 5- or 6-membered carbocyclic or heterocyclic ring, $R^{10}$ is hydrogen, $C_1$–$C_{18}$alkyl, $C_3$- to $C_{24}$cycloalkyl, $C_6$–$C_{10}$aryl or 5- to 7-membered heteroaryl, $R^{14}$ is hydrogen; $C_1$–$C_{18}$alkyl, $C_3$- to $C_{24}$cycloalkyl, $C_1$–$C_4$alkylaryl, each of which i unsubstituted or substituted by cyano groups, hydroxy groups or $C_1$–$C_4$alkoxycarbonyl groups; $C_6$–$C_{10}$aryl which is unsubstituted or substituted by halogen, $C_1$–$C_4$alkyl groups or $C_1$–$C_4$alkoxy groups, or a 5- to 7-membered heterocycle, $R^{15}$ is the radical of a coupling component, or $C_6$–$C_{10}$aryl which is unsubstituted or substituted by halogen, $C_1$–$C_4$alkyl groups or $C_1$–$C_4$alkoxy groups, and X is $C_1$–$C_{37}$alkanediyl, $C_2$–$C_{37}$alkenediyl, $C_2$–$C_{37}$alkynediyl, $C_5$–$C_{12}$cycloalkylene, $C_5$–$C_{12}$cycloalknylene, $C_5$–$C_{12}$cycloalkynylene, a divalent carbocyclic or heterocyclic aromatic radical.

This invention also relates to perylene-3,4-dicarboxylic acid imides of the general formula II

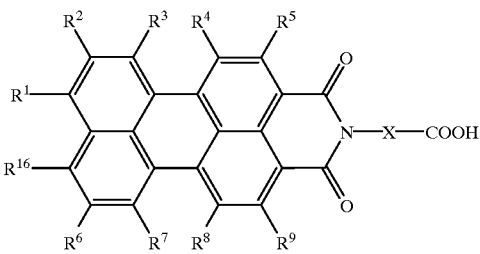

(II)

wherein $R^{16}$ has the same meaning as $R^1$ to $R^9$ and, within the scope of the definition, may be identical to or different from those radicals, as well as to a process for the preparation of the compounds I and II and to their use as colourants.

Perylene-3,4:9,10-tetracarboxylic acid bisimides have been found useful as lightfast colourants. In addition, their use as highly stable fluorescent colourants was opened up by the introduction of solubility-increasing groups (see e.g. EP-A 39085). Owing to their good properties, these colourants are particularly interesting as fluorescent markers, in which case, however, the use of monofunctionalised colourants is required. Moreover, the use of said colourants in homogeneous solution is substantially restricted to non-aqueous media.

J.Phys.Chem. B 101 (1997) 4490–4493 describes di- and tetracarboxylic acid derivatives of perylene. There is no description of a method of preparation for perylene imide monocarboxylic acids.

It is therefore the object of this invention to provide perylene imide derivatives which are monofunctionalised and which are also soluble in aqueous media. In particular, perylene imide monocarboxylic acids are to be provided.

Accordingly, the perylene imide monocarboxylic acids of the general formula I as defined at the outset were found.

In addition, there were found perylene-3,4-dicarboxylic acid imides of the general formula II, acid derivatives of the perylenes I and II, a process for the preparation of the novel compounds as well as their use.

According to this invention, $R^1$, $R^2$, $R^3$, $R^4$, $R^5$, $R^6$, $R^7$, $R^8$, $R^9$ are identical or different and are hydrogen, or one to nine radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, —$OR^{10}$, —CN, —$NR^{11}R^{12}$, —$COR^{13}$, —$NR^{14}COR^{13}$, —$NR^{10}COOR^{13}$, —$NR^{10}CONR^{11}R^{12}$, —$NHSO_2R^{13}$, —$SO_2R^{13}$, —$SOR^{13}$, —$SO_2OR^{13}$, —$CONR^{11}R^{12}$, —$SO_2NR^{11}R^{12}$, —$N=NR^{15}$, —$OCOR^{13}$ and —$OCONHR^{13}$, wherein pairs of adjacent radicals can form a carbocyclic or heterocyclic ring, wherein $R^{13}$ is $C_1$–$C_{18}$alkyl, $C_6$–$C_{10}$aryl, or benzyl which is unsubstituted or substituted by halogen, $C_1$–$C_4$alkyl or $C_1$–$C_4$alkoxy, or a five- to seven-membered heterocyclic radical, $R^{11}$ and $R^{12}$ are each independently of the other hydrogen; $C_1$–$C_{18}$alkyl, $C_3$- to $C_{24}$cycloalkyl, $C_6$–$C_{10}$aryl or 5- to 7-membered heteroaryl, each of which is unsubstituted or substituted by cyano groups or hydroxy groups, or wherein $R^{11}$ and $R^{12}$, together with one of the other radicals $R_2$ to $R_4$, form a 5- or 6-membered carbocyclic or heterocyclic ring, $R^{10}$ is hydrogen, $C_1$–$C_{18}$alkyl, $C_3$- to $C_{24}$cycloalkyl, $C_6$–$C_{10}$aryl or 5- to 7-membered heteroaryl, $R^{14}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxy groups or $C_1$–$C_4$alkoxycarbonyl groups; or $C_6$–$C_{10}$aryl which is substituted by halogen, $C_1$–$C_4$alkyl groups or $C_1$–$C_4$alkoxy groups, or a 5- to 7-membered heterocycle, and $R^{15}$ is the radical of a coupling component, or $C_6$–$C_{10}$aryl which is unsubstituted or substituted by halogen, $C_1$–$C_4$alkyl groups or $C_1$–$C_4$alkoxy groups, with the proviso that $R^1$ is not —$NH_2$.

The unsubstituted or substituted carbocyclic aromatic radical may preferably be mono- to tetracyclic, particularly preferably mono- and bicyclic, radicals containing five to seven carbon atoms per ring, for example phenyl, diphenyl and naphthyl.

The unsubstituted or substituted heterocyclic aromatic radical may preferably be a mono- to tricyclic radical which preferably contains five to seven ring atoms. This radical may consist just of at least one heterocyclic ring, or the heterocyclic ring or rings may contain at least one fused benzene ring. Examples to be mentioned are pyridyl, pyrimidyl, pyrazinyl, triazinyl, furanyl, pyrrolyl, thiophenyl, quinolyl, isoquinolyl, coumarinyl, benzofuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazindionyl, phthalimidyl, chromonyl, naphtholactamyl, benzopyridonyl, ortho-sulfobenzimidyl, maleinimidyl, naphtharidinyl, benzimidazolonyl, benzoxazolonyl, benzothiazolonyl, benzothiazolinyl, quinazolonyl, pyrimidyl, quinoxalonyl, phthalazonyl, dioxapyrinidinyl, pyridonyl, isoquinolonyl, isothiazolyl, benzisoxazolyl, benzisothiazolyl, indazolonyl, acridinyl, acridonyl, quinazolindionyl, benzoxazindionyl, benzoxazinonyl and phthalimidyl.

In a preferred embodiment of this invention, the carbocyclic and/or heterocyclic aromatic radicals are mono- or poly-substituted by customary substituents, particularly preferably by substituents which do not bring about water-sulubility. Examples to be mentioned are:

halogen, typically fluoro, chloro, bromo and iodo, preferably chloro;

the cyano group —CN;

unsubstituted or substituted $C_1$–$C_{18}$alkyl, for example methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tertamyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$alkyl, such as methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, 3-pentyl, 4-heptyl, 3-hexyl, 3-heptyl, very particularly preferably $C_1$–$C_4$alkyl, such as methyl, ethyl, n-propyl, isopropyl, n-butyl, i-butyl, sec-butyl, tert-butyl;

where the cited alkyl groups can be substituted by the following groups which usually do not increase hydrophilicity, for example fluoro, cyano, —$OCOR^{13}$, —$OR^{11}$, —$OCOOR^{13}$, —$CON(R^{11})(R^{12})$ or —$OCONHR^{13}$, wherein $R^{13}$ is $C_1$–$C_{18}$alkyl, such as methyl, ethyl, n-propyl, isopropyl, n-butyl, i-butyl, sec-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, $C_6$–$C_{10}$aryl, such as phenyl, 2,5-di-tert-butylphenyl and naphthyl, preferably phenyl, naphthyl, or benzyl which is unsubstituted or substituted by halogen, such as chloro and fluoro, preferably fluoro, $C_1$–$C_4$alkyl or —O—$C_1$–$C_4$alkyl, or a 5- to 7-membered heterocyclic radical, such as pyridyl, pyrimidyl, pyrazinyl, triazinyl, furanyl, pyrrolyl, thiophenyl, quinolyl, isoquinolyl, coumarinyl, and $R^{11}$ and $R^{12}$ are hydrogen; $C_1$–$C_{18}$alkyl which is unsubstituted or cyano group- or hydroxyl group-substituted as mentioned above, preferably $C_1$–$C_{12}$alkyl, particularly preferably $C_1$–$C_8$alkyl, very particularly preferably $C_1$–$C_4$alkyl, as mentioned above, $C_3$- to $C_{24}$cycloalkyl, preferably $C_5$-, $C_6$-, $C_{12}$-, $C_{15}$-, $C_{16}$-, $C_{20}$- and $C_{24}$cycloalkyl, aryl or heteroaryl, preferably derived from the above-mentioned carbo- and heterocyclic aromatic radicals, in particular phenyl which is unsubstituted or substituted by halogen, $C_1$–$C_4$alkyl or $C_1$–$C_4$alkoxy, or wherein $R^{11}$ and $R^{12}$, together with at least one of the other radicals $R^2$ to $R^9$, form a 5- to 6-membered ring or also a hetero ring, for example a pyridine, pyrrole, furan or pyran ring, preferred —$OR^{11}$ radicals being hydroxy, —O-methyl, —O-ethyl, —O-i-propyl, —O-i-butyl, —O-phenyl, —O-2,5-di-tert-butylphenyl, preferred —$CON(R^{11})(R^{12})$ radicals being —$CONH_2$, —$CONMe_2$, —$CONEt_2$, —$CON(iPr)_2$, —$CON(iBu)_2$, —$CONPh_2$, —$CON(2,5$-di-tert-butylphenyl$)_2$.

In another preferred embodiment of this invention, the substituents at the alkyl groups are mono- or dialkylated amino groups, aryl radicals, for example naphthyl or, preferably, phenyl which is unsubstituted or substituted by halogen, alkyl or —O-alkyl, or also heterocyclic aromatic radicals, such as 2-thienyl, 2-benzoxazolyl, 2-benzothiazolyl, 2-benzimidazolyl, 6-benzimidazolonyl, 2-, 3- or 4-pyridinyl, 2-, 4-, or 6-quinolyl or 1-, 3-, 4-, 6-, or 8-isoquinolyl radicals.

If the cited substituents in turn contain alkyl, then this alkyl can be branched or unbranched and preferably contains 1 to 18, in particular 1 to 12, more preferably 1 to 8 and, particularly preferably, 1 to 4, carbon atoms. Typical examples of unsubstituted alkyl groups are methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl; typical examples of substituted alkyl groups are hydroxymethyl, 2-hydroxyethyl, trifluoromethyl, trifluoroethyl, cyanomethyl, methoxycarbonylmethyl, acetoxymethyl or benzyl.

—$OR^{10}$, wherein $R^{10}$ is hydrogen, $C_1$–$C_{18}$alkyl as defined for $R^{13}$, including the preferred variants cited there, $C_3$- to $C_{24}$cycloalkyl, preferably $C_5$, $C_6$-, $C_{12}$-, $C_{15}$-, $C_{16}$-, $C_{20}$- and $C_{24}$-cycloalkyl, $C_6$–$C_{10}$aryl, such as naphthyl and phenyl, preferably unsubstituted phenyl and phenyl which is substituted by halogen, $C_1$–$C_4$alkyl or $C_1$–$C_4$alkoxy, or 5- to 7-membered heteroaryl. Examples of preferred radicals $R^{10}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl; preferred —$OR^{10}$ radicals are hydroxy, methoxy, —O-ethyl, —O-i-propyl-, —O-i-butyl, —O-phenyl, —O-2,5-di-tert-butylphenyl;

—$NR^{11}R^{12}$, wherein $R^{11}$ and $R^{12}$ have the meanings mentioned above. Examples of preferred radicals to be mentioned are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohexadecylamino, cycloeicosanylamino, cyclotetracosanylamino, phenylamino, N-methylphenylamino, benzylamino, dibenzylamino, piperidyl or morpholyl;

—$COR^{13}$, wherein $R^{13}$ has the meaning cited above. Examples of preferred radicals $R^{13}$ to be mentioned are: methyl, ethyl, n-propyl, isopropyl, n-butyl, sec-butyl, tert-butyl, tertamyl, n-hexyl, 1,1,3,3,-tetramethylbutyl, n-heptyl, n-octyl, n-nonyl, n-decyl, n-undecyl, n-dodecyl, n-octadecyl, 3-pentyl (corresponding to 1-ethyl-n-propyl), 4-heptyl (corresponding to 1-n-propyl-1-n-butyl), 5-nonyl (or: 1-n-butyl-n-pentyl), 6-undecyl (or: 1-ethyl-n-butyl), 7-tridecyl (corresponding to 1-hexylheptyl), 3-hexyl (or: 1-ethyl-n-butyl), 3-heptyl (or: 1-ethyl-n-pentyl), 3-nonyl (or: 1-ethyl-n-heptyl), 3-undecyl (or: 1-ethyl-n-nonyl), hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl;

—$NR^{14}COR^{13}$, wherein $R^{13}$ has the meaning given above, and $R^{14}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$aryl which is unsubstituted or substituted by halogen, $C_1$–$C_4$alkyl groups or by $C_1$–$C_4$alkoxy groups, or a 5- to 7-membered heterocycle, the meaning of the individual radicals, such as alkyl, alkoxy, aryl etc., conforming to the above definitions thereof, including the preferred ranges cited there. Examples of radicals to be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)-phthalimido;

—$NR^{10}COOR^{13}$, wherein $R^{13}$ and $R^{10}$ have the meanings given above. Examples of radicals to be mentioned are: —$NHCOOCH_3$, —$NHCOOC_2H_5$ and —$NHCOOC_6H_5$;

—$NR^{10}CONR^{11}R^{12}$, wherein $R^{11}$, $R^{12}$ and $R^{10}$ have the meanings given above. Examples of radicals to be mentioned are: ureido, N-methylureido, N-phenylureido or N,N'-2',4'-di-methylphenylureido;

—$NHSO_2R^{13}$, wherein $R^{13}$ has the meaning given above. Examples of radicals to be mentioned are: methylsulfonylamino, phenylsulfonylamino, p-tolylsulfonylamino or 2-naphthylsulfonylamino;

—$SO_2R^{13}$, wherein $R^{13}$ has the meaning given above. Examples of radicals to be mentioned are: methylsulfonyl, ethylsulfonyl, phenylsulfonyl, 2-naphthylsulfonyl;

—$SOR^{13}$, wherein $R^{13}$ has the meaning cited above. Radicals to be mentioned as examples are phenylsulfoxidyl and methylsulfoxidyl;

—$SO_2OR^{13}$, wherein $R^{13}$ has the meaning given above. Examples of $R^{13}$ to be mentioned are: methyl, ethyl, phenyl, o-, m- or p-chlorophenyl, o-, m- or p-methylphenyl, 1- or 2-naphthyl;

—$CONR^{11}R^{12}{}_1$ wherein $R^{11}$ and $R^{12}$ have the meanings given above. Examples of radicals to be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperidylcarbamoyl;

—$SO_2NR^{11}R^{12}$, wherein $R^{11}$ and $R^{12}$ have the meanings cited above. Examples of radicals to be mentioned are: sulfamoyl, N-methylsulfamoyl, N-ethylsulfamoyl, N-phenylsulfamoyl, N-methyl-N-phenylsulfamoyl or N-morpholylsulfamoyl;

—$N=NR^{15}$, wherein $R^{15}$ is the radical of a coupling component or a phenyl radical which is unsubstituted or substituted by halogen, alkyl or —O-alkyl, where halogen and alkyl have the meanings given above. Alkyl in the definitions of $R^{15}$ can contain one of the preferred numbers of carbon atoms indicated above. Examples of $R^{15}$ to be mentioned are: the acetoacetarylide, pyrazolyl, pyridonyl, o-, p-hydroxyphenyl, o-hydroxynaphthyl, p-aminophenyl or p-N,N-dimethylaminophenyl radicals.

—$OCOR^{13}$, wherein $R^{13}$ has the meaning cited above. Examples of $R^{13}$ to be mentioned are: methyl, ethyl, phenyl, o-, m- or p-chlorophenyl;

—$OCONHR^{13}$, wherein $R^{13}$ has the meaning cited above. Examples of $R^{13}$ to be mentioned are: methyl, ethyl, phenyl, o-, m- or p-chlorophenyl.

Halogen may be fluoro, chloro, bromo and iodo. Fluoro and chloro are preferred.

Unsubstituted or substituted $C_1$–$C_{18}$alkyl can be: methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, particularly preferably $C_1$–$C_8$alkyl, such as methyl, ethyl, n-propyl, isopropyl, n-butyl, i-butyl, sec-butyl, tert-butyl, tert-amyl, n-hexyl, 1,1,3,3,-tetramethylbutyl, n-heptyl, n-octyl, 3-pentyl, 4-heptyl, 3-hexyl, 3-heptyl, very particularly preferably $C_1$–$C_4$alkyl, such as methyl, ethyl, n-propyl, isopropyl, n-butyl, i-butyl, sec-butyl, tert-butyl;

where the cited alkyl groups can be substituted with the following groups which usually do not increase the hydrophilicity, for example fluoro, hydroxy, cyano, —$OCOR^{13}$, —$OR^{11}$, —$OCOOR^{13}$, —$CON(R^{11})(R^{12})$ or —$OCONHR^{13}$, wherein $R^{18}$ is $C_1$–$C_{18}$alkyl, typically methyl, ethyl, n-propyl, isopropyl, n-butyl, i-butyl, sec-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, preferably $C_1$–$C_{12}$alkyl, such as methyl, ethyl, n-propyl, isopropyl, n-butyl, sec-butyl, tert-butyl, tert-amyl, n-hexyl, n-heptyl, n-octyl, n-nonyl, n-decyl, n-undecyl, n-dodecyl, 3-pentyl, 4-heptyl, 5-nonyl, 6-undecyl, 7-tridecyl, 3-hexyl, 3-heptyl, 3-nonyl, 3-undecyl, $C_6$–$C_{10}$aryl, such as phenyl and naphthyl, preferably naphthyl, or benzyl which is unsubstituted or substituted by halogen, such as chloro and fluoro, preferably fluoro, $C_1$–$C_4$alkyl or —O—$C_1$–$C_4$alkyl, or a 5- to 7-membered heterocyclic radical, such as pyridyl, pyrimidyl, pyrazinyl, triazinyl, furanyl, pyrrolyl, thiophenyl, quinolyl, isoquinolyl, coumarinyl, and $R^{11}$ and $R^{12}$ are hydrogen; $C_1$–$C_{18}$alkyl which is unsubstituted or cyano group- or hydroxyl group-substituted as mentioned above, preferably $C_1$–$C_{12}$alkyl, particularly preferably $C_1$–$C_8$alkyl, very particularly preferably $C_1$–$C_4$alkyl as mentioned above, $C_3$- to $C_{24}$cycloalkyl, preferably $C_5$-, $C_6$-, $C_{12}$-, $C_{15}$-, $C_{16}$-, $C_{20}$- and $C_{24}$cycloalkyl, aryl or heteroaryl, preferably derived from the above-mentioned carbo- and heterocyclic aromatic radicals, in particular phenyl which is unsubstituted or substituted by halogen, $C_1$–$C_4$alkyl or $C_1$–$C_4$alkoxy, or wherein $R^{11}$ and $R^{12}$, together with at least one of the other radicals $R^2$ to $R^9$, form a 5- to 6-membered ring or also a hetero ring, for example a pyridine, pyrrole, furan or pyran ring.

In another preferred embodiment of this invention, the substituents at the alkyl groups are mono- or dialkylated amino groups, aryl radicals, such as naphthyl or, preferably, phenyl which is unsubstituted or substituted by halogen, alkyl or —O-alkyl, or also heterocyclic aromatic radicals, such as the 2-thienyl, 2-benzoxazolyl, 2-benzothiazolyl, 2-benzimidazolyl, 6-benzimidazolonyl, 2-, 3- or 4-pyridinyl, 2-, 4-, or 6-quinolyl or 1-, 3-, 4-, 6-, or 8-isoquinolyl radicals.

If the cited substituents in turn contain alkyl, then this alkyl can be branched or unbranched and preferably contains 1 to 18, in particular 1 to 12, more preferably 1 to 8 and, particularly preferably, 1 to 4, carbon atoms. Typical examples of unsubstituted alkyl groups are methyl, ethyl, n-propyl, isopropyl, n-butyl, sec-butyl, tertbutyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, and typical examples of substituted alkyl groups are hydroxymethyl, 2-hydroxyethyl, trifluoromethyl, trifluoroethyl, cyanomethyl, methoxycarbonylmethyl, acetoxymethyl or benzyl.

$R^{10}$ in —$OR^{10}$ can be: hydrogen, $C_1$–$C_{18}$alkyl as defined above for $R^{13}$, including the preferred variants mentioned there. Examples of preferred radicals $R^{10}$ to be mentioned are: methyl, ethyl, n-propyl, isopropyl, n-butyl, sec- butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl and pyranylmethyl. Examples of preferred —$OR^{10}$ radicals are: hydroxy, methoxy, —O-ethyl, —O-i-propyl-, —O-i-butyl, —O-phenyl, —O-2,5-di-tertbutylphenyl.

$R^{11}$ and $R^{12}$ in —$NR^{11}R^{12}$ can be the radicals defined above. Typical examples of preferred radicals are: amino, methylamino, dimethylamino, ethylamino, diethylamino, isopropylamino, 2-hydroxyethylamino, 2-hydroxypropylamino, N,N-bis(2-hydroxyethyl)amino, cyclopentylamino, cyclohexylamino, cyclododecylamino, cyclopentadecylamino, cyclohecadecylamino, cycloeicosanylamino, cyclotetracosanylamino, phenylamino, N-methylphenylamino, benzylamino, dibenzylamino, piperidyl or morpholyl and, particularly preferably, dimethylamino, diethylamino, di-n-propylamino, di-n-butylamino, di-n-pentylamino, di-n-hexylamino, di-n-heptylamino, di-n-octylamino, di-n-dodecylamino.

$R^{11}$ and $R^{12}$ on their own or together with at least one of the other free radicals selected from $R^2$, $R^3$, $R^4$, $R^5$, $R^6$, $R^7$, $R^8$, $R^9$ can form one or several 5- or 6-membered saturated or unsaturated rings, typically pyridine, pyrrole, piperidine, quinoline or benzoquinolizine derivatives.

Suitable —$COR^{13}$ radicals can be those, wherein $R^{13}$ has the meaning given above. Examples of preferred radicals $R^{13}$ to be mentioned are: methyl, ethyl, n-propyl, isopropyl, n-butyl, sec-butyl, tert-butyl, tert-amyl, n-hexyl, 1,1,3,3,-tetramethylbutyl, n-heptyl, n-octyl, n-nonyl, n-decyl, n-undecyl, n-dodecyl, n-octadecyl, 3-pentyl, 4-heptyl, 5-nonyl, 6-undecyl, 7-tridecyl, 3-hexyl, 3-heptyl, 3-nonyl, 3-undecyl, hydroxymethyl, 2-hydroxyethyl, trifluoromethyl, trifluoroethyl, cyanomethyl, methoxycarbonylmethyl, acetoxymethyl, benzyl, phenyl, o-, m- or p-chlorophenyl, o-, m-, or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl and furfuryl.

—$NR^{10}COR^{13}$ radicals can be those, wherein $R^{13}$ has the meaning given above and $R^{14}$ is hydrogen; $C_1$–$C_{18}$alkyl, $C_3$- to $C_{24}$cycloalkyl, $C_1$–$C_4$alkylaryl, each of which is unsubstituted or substituted by cyano groups, hydroxyl groups or $C_1$–$C_4$alkoxycarbonyl groups; $C_6$–$C_{10}$aryl which is unsubstituted or substituted by halogen, $C_1$–$C_4$alkyl groups or by $C_1$–$C_4$alkoxy groups, or a 5- to 7-membered heterocycle, the meaning of the individual radicals, such as alkyl, alkoxy, aryl etc., conforming to the above definitions thereof, including the preferred ranges cited there, for example o-, m- or p-chlorophenyl, o-, m- or p-methylphenyl, 1- or 2-naphthyl, cyclopentyl, cyclohexyl, cyclododecyl, cyclopentadecyl, cyclohexadecyl, cycloeicosanyl, cyclotetracosanyl, thienyl, pyranylmethyl, benzyl or furfuryl. Examples of radicals to be mentioned are: acetylamino, propionylamino, butyrylamino, benzoylamino, p-chlorobenzoylamino, p-methylbenzoylamino, N-methylacetamino, N-methylbenzoylamino, N-succinimido, N-phthalimido or N-(4-amino)phthalimido.

—$NR^{10}COOR^{13}$ radicals can be those, wherein $R^{13}$ and $R^{10}$ have the meanings cited above. Examples to be mentioned are: —$NHCOOCH_3$, —$NHCOOC_2H_5$ and —$NHCOOC_6H_5$.

—$NR^{10}CONR^{11}R^{12}$ radicals can be those, wherein $R^{11}$, $R^{12}$ and $R^{10}$ have the meanings given above. Examples of radicals to be mentioned are: ureido, N-methylureido, N-phenylureido or N,N'-2',4'-dimethylphenylureido.

—$NHSO_2R^{13}$ radicals can be those, wherein $R^{13}$ has the meaning given above. Examples of radicals to be mentioned are: methylsulfonylamino, phenylsulfonylamino, p-tolylsulfonylamino or 2-naphthylsulfonylamino.

—SO$_2$R$^{13}$ radicals can be those, wherein R$^{13}$ has the meaning given above. Examples of radicals to be mentioned are: methylsulfonyl, ethylsulfonyl, phenylsulfonyl, 2-naphthylsulfonyl.

—SOR$^{13}$ radicals can be those, wherein R$^{13}$ has the meaning given above. Radicals to be mentioned as examples are phenylsulfoxidyl and methylsulfoxidyl.

—SO$_2$OR$^{13}$ radicals can be those, wherein R$^{13}$ has the meaning given above. Examples of R$^{13}$ are: methyl, ethyl, phenyl, o-, m- or p-chlorophenyl, o-, m- or p-methylphenyl, 1- or 2-naphthyl.

—CONR$^{11}$R$^{12}$ radicals can be those, wherein R$^{12}$ and R$^{12}$ have the meanings cited above. Examples of radicals to be mentioned are: carbamoyl, N-methylcarbamoyl, N-ethylcarbamoyl, N-phenylcarbamoyl, N,N-dimethylcarbamoyl, N-methyl-N-phenylcarbamoyl, N-1-naphthylcarbamoyl or N-piperidylcarbamoyl.

—SO$_2$NR$^{11}$R$^{12}$ radicals can be those, wherein R$^{11}$ and R$^{12}$ have the meanings given above. Examples of radicals to be mentioned are: sulfamoyl, N-methylsulfamoyl, N-ethylsulfamoyl, N-phenylsulfamoyl, N-methyl-N-phenylsulfamoyl or N-morpholylsulfamoyl.

—N=NR$^{15}$ radicals can be those, wherein R$^{15}$ is the radical of a coupling component or a phenyl radical which is unsubstituted or substituted by halogen, alkyl or —O-alkyl, wherein halogen and alkyl have the meanings given above. Alkyl in the definitions of R$^{15}$ can contain one of the preferred numbers of carbon atoms indicated above. Examples of R$^{15}$ to be mentioned are: the acetoacetarylide, pyrazolyl, pyridonyl, o-, p-hydroxyphenyl, o-hydroxynaphthyl, p-aminophenyl or p-N,N-dimethylaminophenyl radicals.

—OCOR$^{13}$ radicals can be those, wherein R$^{13}$ has the meaning cited above. Examples of R$^{13}$ to be mentioned are: methyl, ethyl, phenyl, o-, m- or p-chlorophenyl.

—OCONHR$^{13}$ radicals can be those, wherein R$^{13}$ has the meaning cited above. Examples of R$^{13}$ to be mentioned are: methyl, ethyl, phenyl, o-, m- or p-chlorophenyl.

X may be C$_1$–C$_{37}$alkandiyl, for example methylene, 1,1-, 1,2-ethanediyl, 1,1-, 1,2-, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, 1,16-hexadecanediyl, 1,17-heptadecanediyl, 1,18-octadecanediyl, 1,19-nonadecanediyl, 1,20-eicosanediyl, 1,21-heneicosanediyl, 1,22-docosanediyl, 1,23-tricosanediyl, 1,24-tetracosanediyl, 1,25-pentacosanediyl, 1,26-hexacosanediyl, 1,27-heptacosanediyl, 1,28-octacosanediyl, 1,29-nonacosanediyl, 1,30-triacontanediyl, 1,31-hentriacontanediyl, 1,32-dotriacontanediyl, 1,33-tritriacontanediyl, 1,34-tetratriacontanediyl, 1,35-pentatriacontanediyl, 1,36-hexatriacontanediyl, 1,37-heptatriacontanediyl, preferably C$_1$–C$_{18}$alkanediyl, such as methylene, 1,1-, 1,2-ethanediyl, 1,1-, 1,2-, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, 1,16-hexadecanediyl, 1,17-heptadecanediyl, 1,18-octadecanediyl, C$_2$–C$_{37}$alkenediyl, such as 1,1-, 1,2-ethenediyl, 1,2-, 1,2-, 1,3-propenylene, 1,4-butylene, 1,5-pentenylene, 1,6-hexenylene, 1,7-heptenylene, 1,8-octenylene, 1,9-nonenylene, 1,1 0-decenylene, 1,11-undecenylene, 1,12-dodecenylene, 1,13-tridecenylene, 1,14-tetradecenylene, 1,15-pentadecenylene, 1,16-hexadecenylene, 1,17-heptadecenylene, 1,18-octadecenylene, 1,19-nonadecenylene, 1,20-eicosenylene, 1,21-heneicosenylene, 1,22-docosenylene, 1,23-tricosenylene, 1,24-tetracosenylene, 1,25-pentacosenylene, 1,26-hexacosenylene, 1,27-heptacosenylene, 1,28-octacosenylene, 1,29-nonacosenylene, 1,30-triacontenylene, 1,31-hentriacontenylene, 1,32-dotriacontenylene, 1,33-tritriacontenylene, 1,34-tetratriacontenylene, 1,35-pentatriacontenylene, 1,36-hexatriacontenylene, 1,37-heptatriacontenylene, preferably C$_2$–C$_{18}$alkenylene, such as 1,1-, 1,2-ethenylene, 1,2-, 1,2-, 1,3-propenylene, 1,4-butenylene, 1,5-pentenylene, 1,6-hexenylene, 1,7-heptenylene, 1,8-octenylene, 1,9-nonenylene, 1,10-decenylene, 1,11 -undecenylene, 1,12-dodecenylene, 1,13-tridecenylene, 1,14-tetradecenylene, 1,15-pentadecenylene, 1,16-hexadecenylene, 1,17-heptadecenylene, 1,18-octadecenylene, C$_2$–C$_{37}$alkynylene, such as 1,1-, 1,2-ethynylene, 1,2-, 1,2-, 1,3-propynylene, 1,4-butylene, 1,5-pentynylene, 1,6-hexynylene, 1,7-heptynylene, 1,8-octynylene, 1,9-nonynylene, 1,10-decynylene, 1,11-undecynylene, 1,12-dodecynylene, 1,13-tridecynylene, 1,14-tetradecynylene, 1,15-pentadecynylene, 1,16-hexadecynylene, 1,17-heptadecynylene, 1,18-octadecynylene, 1,19-nonadecynylene, 1,20-eicosynylene, 1,21-heneicosynylene, 1,22-docosynylene, 1,23-tricosynylene, 1,24-tetracosynylene, 1,25-pentacosynylene, 1,26-hexacosynylene, 1,27-heptacosynylene, 1,28-octacosynylene, 1,29-nonacosynylene, 1,30-triacontynylene, 1,31-hentriacontynylene, 1,32-dotriacontynylene, 1,33-tritriacontynylene, 1,34-tetratriacontynylene, 1,35-pentatriacontynylene, 1,36-hexatriacontynylene, 1,37-heptatriacontynylene, preferably C$_2$–C$_{18}$alkynylene, such as 1,1-, 1,2-ethynylene, 1,2-, 1,2-, 1,3-propynylene, 1,4-butynylene, 1,5-pentynylene, 1,6-hexynylene, 1,7-heptynylene, 1,8-octynylene, 1,9-nonynylene, 1,10-decynylene, 1,11-undecynylene, 1,12-dodecynylene, 1,13-tridecynylene, 1,14-tetradecynylene, 1,15-pentadecynylene, 1,16-hexadecynylene, 1,17-heptadecynylene, 1,18-octadecynylene, C$_3$–C$_{12}$cycloalkylene, such as 1,1-, 1,2-cyclopropylene, 1,1-, 1,2-, 1,3-cyclobutylene, 1,1-, 1,2-, 1,3-cyclopentylene, 1,1-, 1,2-, 1,3-cyclohexylene, 1,1-, 1,2-, 1,3-cycloheptylene, 1,1-, 1,2-, 1,3-,1,4-cyclooctylene, 1,1-, 1,2-, 1,3-, 1,4-cyclononylene, 1,1-, 1,2-, 1,3-, 1,4-, 1,5-cyclodecylene, 1,1-, 1,2-, 1,3-, 1,4-, 1,5-, cycloundecylene, 1,1-, 1,2-, 1,3-, 1,4-, 1,5-cyclododecylene, preferably 1,1-, 1,2-, 1,3-cyclopentylene, 1,1-, 1,2-,1,3-cyclohexylene, 1,1-, 1,2-,1,3-cycloheptylene, 1,1-, 1,2-,1,3-, 1,4-, cyclooctylene, C$_6$–C$_{12}$cycloalkenylene, such as 1,1-, 1,2-, 1,3-cyclohexenylene, 1,1-, 1,2-, 1,3-, cycloheptenylene, 1,1-, 1,2-, 1,3-,1,4-cyclooctenylene, 1,1-, 1,2-, 1,3-,1,4-cyclononenylene, 1,1-, 1,2-, 1,3-, 1,4-, 1,5-cyclodecenylene, 1,1-, 1,2-, 1,3-, 1,4-, 1,5-cycloundecenylene, 1,1-, 1,2-, 1,3-, 1,4-, 1,5-cyclododecenylene, preferably 1,1-, 1,2-, 1,3-cyclopentenylene, 1,1-, 1,2-, 1,3-cyclohexenylene, 1,1-, 1,2-, 1,3-cycloheptenylene, 1,1-, 1,2-, 1,3-,1,4-cyclooctenylene, C$_6$–C$_{12}$cycloalkynylene, such as 1,1-, 1,2-, 1,3-cyclohexynylene, 1,1-, 1,2-, 1,3-cycloheptynylene, 1,1-, 1,2-, 1,3-,1,4-cyclooctynylene, 1,1-, 1,2-, 1,3-, 1,4-cyclononynylene, 1,1-, 1,2-, 1,3-, 1,4-, 1,5-cyclodecynylene, 1,1-, 1,2-, 1,3-, 1,4-, 1,5-cycloundecynylene, 1,1-, 1,2-, 1,3-, 1,4-, 1,5-cyclododecynylene, preferably 1,1-, 1,2-, 1,3-cyclopentynylene, 1,1-, 1,2-, 1,3 -cyclohexynylene, 1,1-, 1,2-, 1,3-cycloheptynylene, 1,1-, 1,2-, 1,3-,1,4-cyclooctynylene, a carbocyclic aromatic radical, such as $C_6$–$C_{20}$aryl, preferably phenyl, such as 1,2-, 1,3-, 1,4-phenylene, particularly preferably 1,4-phenylene, 1,2-, 1,3-, 1,4-, 1,5-, 1,6-naphthylene, 1,8-naphthylene, 2,3-naphthylene, 2,6-naphthylene, 2,7-naphthylene, 1,2-anthrylene, 1,3-anthrylene, 1,4-anthrylene, 1,5-anthrylene 1,6-anthrylene, 1,7-anthrylene, 1,8-anthrylene, 1,9-anthrylene, 1,10-anthrylene, 2,3-anthrylene, 2,6-anthrylene, 2,7-anthrylene, 2,9-anthrylene, 2,10-anthrylene, 1,2-phenanthrylene, 9,10-phenanthrylene, 4,4'-biphenylylene, 1,2-perylenylene, 3,4-perylenylene, 3,9-perylenylene, 3,10-perylenylene, 1,2-pyrenylene, 3,5-pyrenylene, 3,8-pyrenylene, 3,10-pyrenylene, 4,9-pyrenylene, or a heterocyclic aromatic radical, such as 3,4-thiophenylene, 3,5-thiophenylene, 3,6-thiophenylene, 4,5-thiophenylene, 1,2-pyrrolylene, 1,3-pyrrolylene, 1,4-pyrrolylene, 1,5-pyrrolylene, 3,4-pyrrolylene, 3,5-pyrrolylene, 3,6-pyrrolylene, 4,5-pyrrolylene, 3,4-furanylene, 3,5-furanylene, 3,6-furanylene, 4,5-furanylene, 2,3-pyridinylene, 2,4-pyridinylene, 2,5-pyridinylene, 2,6-pyridinylene, 3,4-pyridinylene, 3,5-pyridinylene, 1,2-indolylenylene, 1,3-indolylenylene, 1,5-indolylenylene, 1,6-indolylenylene, 1,7-indolylenylene, 2,3-indolylenylene, 2,4-indolylenylene, 2,5-indolylenylene, 2,6-indolylenylene, 2,7-indolylenylene, 3,4-indolylenylene, 3,5-indolylenylene, 3,6-indolylenylene, 3,7-indolylenylene, 4,5-indolylenylene, 4,6-indolylenylene, 4,7-indolylenylene, 5,6-indolylenylene, 5,7-indolylenylene, 6,7-indolylenylene, 2,3-quinolylene, 2,4-quinolylene, 2,5-quinolylene, 2,6-quinolylene, 2,7-quinolylene, 2,8-quinolylene, 3,4-quinolylene, 3,5-quinolylene, 3,6-quinolylene, 3,7-quinolylene, 3,8-quinolylene, 4,5-quinolylene, 4,6-quinolylene, 4,7-quinolylene, 4,8-quinolylene, 5,6-quinolylene, 5,7-quinolylene, 5,8-quinolylene, 6,7-quinolylene, 6,8-quinolylene, 7,8-quinolylene, 1,3-isoquinolylene, 1,4-isoquinolylene, 1,5-isoquinolylene, 1,6-isoquinolylene, 1,7-isoquinolylene, 1,8-isoquinolylene, 3,4-isoquinolylene, 3,5-isoquinolylene, 3,6-isoquinolylene, 3,7-isoquinolylene, 3,8-isoquinolylene, 4,5-isoquinolylene, 4,6-isoquinolylene, 4,7-isoquinolylene, 4,8-isoquinolylene, 5,6-isoquinolylene, 5,7-isoquinolylene, 5,8-isoquinolylene, 6,7-isoquinolylene, 6,8-isoquinolylene, 7,8-isoquinolylene.

Particularly preferred perylene-3,4:9,10-tetracarboxylic acid imides of the general formula I are those, wherein $R^2$, $R^3$, $R^4$, $R^5$, $R^6$, $R^7$, $R^8$ and $R^9$ are hydrogen, $R^1$ is a secondary alkyl radical, such as 1-($C_1$–$C_9$alkyl)-$C_2$–$C_{10}$alkyl, in particular those, wherein $R^1$ has a "swallowtail structure", for example 1-methylethyl, 1-ethyl-n-propyl, 1-n-propyl-n-butyl, 1-n-butyl-n-pentyl, 1-n-hexyl-1-heptyl, 1-n-heptyl-1-n-octyl, 1-n-octyl-1-n-nonyl, 1-n-nonyl-1-decyl, and also aromatic radicals, preferably phenyl radicals, very particularly preferably $C_1$–$C_6$alkyl-substituted phenyl such as 2,6-di-tert-butylphenyl and 2,5-di-tert-butylphenyl, and X is phenylene, preferably 1,4-phenylene, $C_1$–$C_{18}$alkylene, preferably 1,2-ethylene, 1,4-butylene, 1,6-hexylene, and 1,11-undecylene.

The novel perylene monocarboxylic acids I are preferably obtained by reacting perylene anhydride imides of the general formula III

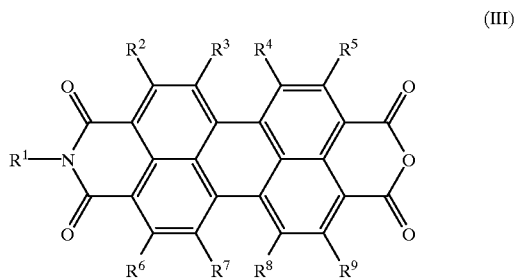

with an amino acid of formula IV

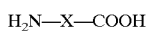        IV.

This invention thus also relates to a process for the preparation of perylene imides, which comprises reacting a perylene anhydride imide with a primary amine at elevated temperature, the perylene anhydride imide III being reacted with an amino acid IV. The reaction is preferably carried out at reaction temperatures in the range from 80 to 150, particularly preferably from 100 to 130° C. According to findings to date, the success of the reaction does not depend on the choice of the pressure range. For the sake of simplicity, the reaction is usually carried out at atmospheric pressure, but it is also possible to choose lower pressure ranges of up to 10 kPa or of up to 10 Mpa. The reaction times are preferably chosen in the range from 30 min to 2.5 h, depending on the chosen reaction temperature.

In an another preferred embodiment of this invention, the reaction is carried out in the presence of a basic organic solvent, preferably in the presence of a nitrogen-containing heterocycle such as imidazole, quinoline, pyridine, picoline or N-methylpyrrolidone, particularly preferably imidazole or quinoline. The reaction can also be carried out using a glycol, such as ethylene glycol or diethylene glycol. The amount of base used is usually chosen in the range from 0.1 to 1 mol per 1 kg solvent, preferably 0.1 to 0.5 mol per kg solvent.

In a particularly preferred embodiment of this invention, the reaction is carried out in melted imidazole at a temperature in the range from 100 to 130° C. According to findings to date, the novel perylene imide monocarboxylic acid I and the perylene-3,4-dicarboxylic acid imides II are particularly successfully prepared in a pure state.

In another preferred embodiment of this invention, the reaction is carried out in a protective gas atmosphere. Preferred protective gases are, for example, nitrogen and the noble gases, such as helium or argon.

The amino acid IV is usually used in excess, preferably in a molar ratio of 1.1:1 to 20:1, particularly preferably of 1.3:1 to 15:1 (amino acid IV: perylene anhydride imide III).

It may futhermore be advantageous to carry out the reaction in the presence of heavy metal salts, for example the zinc, lead, calcium, copper, manganese, iron, cobalt, nickel, tin, silver or magnesium salts, such as chlorides, sulfates, nitrates or acetates, preferably water-soluble zinc salts, such as zinc acetate and zinc chloride. The molar ratio of perylene anhydride imide III to heavy metal salt is usually chosen in the range from 10:1 to 1:10, preferably from 2.5:1 to 1:2.5.

Perylene-3,4:9,10-tetracarboxylic acid monoanhydride monoimides of formula III are known or can be prepared by known methods, for example by (a) reacting the corresponding known bisanhydrides with a primary amine, or (b) by reacting, in a first step, a perylene bisanhydride with a primary amine to a perylene bisimide, which is then saponified, preferably alkaline, in a second step to the corresponding perylene anhydride imide. Some compounds and their preparation are described, for example, in Chem. Ber. 124 (1991) 529.

Preferred perylene anhydride imides III are those, wherein $R^1$ is an aliphatic radical as defined above, preferably a secondary alkyl radical such as 1-($C_1$–$C_9$alkyl)-$C_2$–$C_{10}$alkyl, $R^1$ preferably having a "swallowtail structure" which may be realised with radicals such as 1-methylethyl, 1-ethyl-n-propyl, 1-n-propyl-n-butyl, 1-n-butyl-n-pentyl, 1-n-hexyl-1-n-heptyl, 1-n-heptyl-1-n-octyl, 1-n-octyl-1-n-nonyl, 1-n-nonyl-1-n-decyl.

Amino acids IV can, in principle, be all known amino acids as long as they do not interfere with the desired reaction. Those amino acids IV are preferred, wherein X is $C_1$–$C_{37}$alkanediyl, such as methylene, 1,1-, 1,2-ethanediyl, 1,1-, 1,2-, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, 1,16-hexadecanediyl, 1,17-heptadecanediyl, 1,18-octadecanediyl, 1,19-nonadecanediyl, 1,20-eicosanediyl, 1,21-heneicosanediyl, 1,22-docosanediyl, 1,23-tricosanediyl, 1,24-tetracosanediyl, 1,25-pentacosanediyl, 1,26-hexacosanediyl, 1,27-heptacosanediyl, 1,28-octacosanediyl, 1,29-nonacosanediyl, 1,30-triacontanediyl, 1,31-hentriacontanediyl, 1,32-dotriacontanediyl, 1,33-tritriacontanediyl, 1,34-tetratriacontanediyl, 1,35-pentatriacontanediyl, 1,36-hexatriacontanediyl, 1,37-heptatriacontanediyl, preferably $C_1$–$C_{18}$alkanediyl, such as methylene, 1,1-, 1,2-ethanediyl, 1,1-, 1,2-, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, 1,13-tridecanediyl, 1,14-tetradecanediyl, 1,15-pentadecanediyl, 1,16-hexadecanediyl, 1,17-heptadecanediyl, 1,18-octadecanediyl, $C_2$–$C_{37}$alkenediyl, such as 1,1-, 1,2-ethenediyl, 1,2-, 1,2-, 1,3-propenylene, 1,4-butylene, 1,5-pentenylene, 1,6-hexenylene, 1,7-heptenylene, 1,8-octenylene, 1,9-nonenylene, 1,10-decenylene, 1,11-undecenylene, 1,12-dodecenylene, 1,13-tridecenylene, 1,14-tetradecenylene, 1,15-pentadecenylene, 1,16-hexadecenylene, 1,17-heptadecenylene, 1,18-octadecenylene, 1,19-nonadecenylene, 1,20-eicosenylene, 1,21-heneicosenylene, 1,22-docosenylene, 1,23-tricosenylene, 1,24-tetracosenylene, 1,25-pentacosenylene, 1,26-hexacosenylene, 1,27-heptacosenylene, 1,28-octacosenylene, 1,29-nonacosenylene, 1,30-triacontenylene, 1,31-hentriacontenylene, 1,32-dotriacontenylene, 1,33-tritriacontenylene, 1,34-tetratriacontenylene, 1,35-pentatriacontenylene, 1,36-hexatriacontenylene, 1,37-heptatriacontenylene, preferably $C_1$–$C_{18}$alkenylene, such as 1,1-, 1,2-ethenylene, 1,2-, 1,2-, 1,3-propenylene, 1,4-butenylene, 1,5-pentenylene, 1,6-hexenylene, 1,7-heptenylene, 1,8-octenylene, 1,9-nonenylene, 1,10-decenylene, 1,11-undecenylene, 1,12-dodecenylene, 1,13-tridecenylene, 1,14-tetradecenylene, 1,15-pentadecenylene, 1,16-hexadecenylene, 1,17-heptadecenylene, 1,18-octadecenylene, $C_{2-C37}$alkynylene, such as 1,1-, 1,2-ethynylene, 1,2-, 1,2-, 1,3-propynylene, 1,4-butynylene, 1,5-pentynylene, 1,6-hexynylene, 1,7-heptynylene, 1,8-octynylene, 1,9-nonynylene, 1,10-decynylene, 1,11-undecynylene, 1,12-dodecynylene, 1,13-tridecynylene, 1,14-tetradecynylene, 1,15-pentadecynylene, 1,16-hexadecynylene, 1,17-heptadecynylene, 1,18-octadecynylene, 1,19-nonadecynylene, 1,20-eicosynylene, 1,21-heneicosynylene, 1,22-docosynylene, 1,23-tricosynylene, 1,24-tetracosynylene, 1,25-pentacosynylene, 1,26-hexacosynylene, 1,27-heptacosynylene, 1,28-octacosynylene, 1,29-nonacosynylene, 1,30-triacontynylene, 1,31-hentriacontynylene, 1,32-dotriacontynylene, 1,33-tritriacontynylene, 1,34-tetratriacontynylene, 1,35-pentatriacontynylene, 1,36-hexatriacontynylene, 1,37-heptatriacontynylene, preferably $C_2$–$C_{18}$alkynylene, such as 1,1-, 1,2-ethynylene, 1,2-, 1,2-, 1,3-propynylene, 1,4-butynylene, 1,5-pentynylene, 1,6-hexynylene, 1,7-heptynylene, 1,8-octynylene, 1,9-nonynylene, 1,10-decynylene, 1,11-undecynylene, 1,12-dodecynylene, 1,13-tridecynylene, 1,14-tetradecynylene, 1,15-pentadecynylene, 1,16-hexadecynylene, 1,17-heptadecynylene, 1,18-octadecynylene, $C_3$–$C_{12}$cycloalkylene, such as 1,1-, 1,2-cyclopropylene, 1,1-, 1,2-, 1,3-cyclobutylene, 1,1-, 1,2-, 1,3-cyclopentylene, 1,1-, 1,2-, 1,3-cyclohexylene, 1,1-, 1,2-, 1,3-cycloheptylene, 1,1-, 1,2-, 1,3-,1,4-cyclooctylene, 1,1-, 1,2-, 1,3-, 1,4-cyclononylene, 1,1-, 1,2-, 1,3-, 1,4-, 1,5-cyclodecylene, 1,1-, 1,2-, 1,3-, 1,4-, 1,5-cycloundecylene, 1,1-, 1,2-, 1,3-, 1,4-, 1,5-cyclododecylene, preferably 1,1-, 1,2-, 1,3-cyclopentylene, 1,1-, 1,2-, 1,3-cyclohexylene, 1,1-, 1,2-, 1,3-cycloheptylene, 1,1-, 1,2-, 1,3-, 1,4-cyclooctylene, $C_6$–$C_{12}$cycloalkenylene, such as 1,1-, 1,2-, 1,3-cyclohexenylene, 1,1-, 1,2-1,3-cycloheptenylene, 1,1-, 1,2-, 1,3-,1,4-cyclooctenylene, 1,1-, 1,2-, 1,3-, 1,4-cyclononenylene, 1,1-, 1,2-, 1,3-, 1,4-, 1,5-cyclodecenylene, 1,1-, 1,2-, 1,3-, 1,4-, 1,5-cycloundecenylene, 1,1-, 1,2-, 1,3-, 1,4-, 1,5-cyclododecenylene, preferably 1,1-, 1,2-, 1,3-cyclopentenylene, 1,1-, 1,2-, 1,3-cyclohexenylene, 1,1-, 1,2-, 1,3-cycloheptenylene, 1,1-, 1,2-, 1,3-,1,4-cyclooctenylene, $C_6$–$C_{12}$cycloalkynylene, such as 1,1-, 1,2-, 1,3-cyclohexynylene 1,1-, 1,2-, 1,3-cycloheptynylene, 1,1-, 1,2-, 1,3-,1,4-cyclooctynylene, 1,1-, 1,2-, 1,3-, 1,4-cyclononynylene, 1,1-, 1,2-, 1,3-, 1,4-, 1,5-cyclodecynylene, 1,1-, 1,2-, 1,3-, 1,4-, 1,5-cycloundecynylene, 1,1-, 1,2-, 1,3-, 1,4-,1,5-cyclododecynylene, preferably 1,1-, 1,2-, 1,3-cyclopentynylene, 1,1-, 1,2-, 1,3-cyclohexynylene, 1,1-, 1,2-,1,3-cycloheptynylene, 1,1-, 1,2-, 1,3-,1,4-cyclooctynylene, a carbocyclic aromatic radical, such as $C_6$–$C_{20}$aryl, preferably phenyl, such as 1,2-, 1,3-, 1,4-phenylene, particularly preferably 1,4-phenylene, 1,2-, 1,3-, 1,4-, 1,5-, 1,6-naphthylene, 1,8-naphthylene, 2,3-naphthylene, 2,6-naphthylene, 2,7-naphthylene, 1,2-anthrylene, 1,3-anthrylene, 1,4-anthrylene, 1,5-anthrylene 1,6-anthrylene, 1,7-anthrylene, 1,8-anthrylene, 1,9-anthrylene, 1,10-anthrylene, 2,3-anthrylene, 2,6-anthrylene, 2,7-anthrylene, 2,9-anthrylene, 2,10-anthrylene, 1,2-phenanthrylene, 9,10-phenanthrylene, 4,4'-biphenylylene, 1,2-perylenylene, 3,4-perylenylene, 3,9-perylenylene, 3,10-perylenylene, 1,2-pyrenylene, 3,5-pyrenylene, 3,8-pyrenylene, 3,10-pyrenylene, 4,9-pyrenylene, or a heterocyclic aromatic radical, such as 3,4-thiophenylene, 3,5-thiophenylene, 3,6-thiophenylene, 4,5-thiophenylene, 1,2-pyrrolylene, 1,3-pyrrolylene, 1,4-pyrrolylene, 1,5-pyrrolylene, 3,4-pyrrolylene, 3,5-pyrrolylene, 3,6-pyrrolylene, 4,5-pyrrolylene, 3,4-furanylene, 3,5-furanylene, 3,6-furanylene, 4,5-furanylene, 2,3-pyridinylene, 2,4-pyridinylene, 2,5-pyridinylene, 2,6-pyridinylene, 3,4-pyridinylene, 3,5-pyridinylene, 1,2-indolylenylene, 1,3-indolylenylene, 1,5-indolylenylene, 1,6-indolylenylene, 1,7-indolylenylene, 2,3-indolylenylene, 2,4-indolylenylene, 2,5-indolylenylene, 2,6-indolylenylene, 2,7-indolylenylene, 3,4-indolylenylene, 3,5-indolylenylene, 3,6-indolylenylene, 3,7-indolylenylene, 4,5-indolylenylene, 4,6- indolylenylene, 4,7-indolylenylene, 5,6-indolylenylene, 5,7-indolylenylene, 6,7-indolylenylene, 2,3-quinolylene, 2,4-quinolylene, 2,5-quinolylene, 2,6-quinolylene, 2,7-quinolylene, 2,8-quinolylene, 3,4-quinolylene, 3,5-quinolylene, 3,6-quinolylene, 3,7-quinolylene, 3,8-quinolylene, 4,5-quinolylene, 4,6-quinolylene, 4,7-quinolylene, 4,8-quinolylene, 5,6-quinolylene, 5,7-quinolylene, 5,8-quinolylene, 6,7-quinolylene, 6,8-quinolylene, 7,8-quinolylene, 1,3-isoquinolylene, 1,4-isoquinolylene, 1,5-isoquinolylene, 1,6-isoquinolylene, 1,7-isoquinolylene, 1,8-isoquinolylene, 3,4-isoquinolylene, 3,5-isoquinolylene, 3,6-isoquinolylene, 3,7-isoquinolylene, 3,8-isoquinolylene, 4,5-isoquinolylene, 4,6-isoquinolylene, 4,7-isoquinolylene, 4,8-isoquinolylene, 5,6-isoquinolylene, 5,7-isoquinolylene, 5,8-isoquinolylene, 6,7-isoquinolylene, 6,8-isoquinolylene, 7,8-isoquinolylene.

Particularly preferred amino acids IV are 4-aminobenzoic acid, 3-aminobenzoic acid, 2-aminobenzoic acid, the natural amino acids containing a primary amino group, such as glycine, β-alanine, histidine, leucine, ornithine, phenylalanine, tryptophane or valine, 4-aminobutyric acid, 6-aminocaproic acid and 11-aminoundecanoic acid.

The novel perylene derivates I can be purified and isolated by customary methods, for example by chromatography, preferably column chromatography, or by extractive recrystallisation. The perylene derivatives I can then usually be used directly for further reactions.

A particularly preferred embodiment of this invention relates to the working up of the reaction mixture, adding prior to the customary purification steps an acid to the reaction mixture, preferably a mineral acid, particularly preferably a semi-concentrated, for example 1.5 to 3N, preferably 2N, mineral acid, or a concentrated mineral acid, for example semi-concentrated, preferably 2N, hydrochloric acid, or concentrated hydrochloric acid.

The amount of acid used usually depends on the choice of the substituents and the strength and kind of acid used. The acid is usually added in excess amount. When using 2N HCl, the amount of acid used is typically in the range from 100 to 1000 l per mol of perylene anhydride imide III used.

When working up the novel perylenes I, the customary treatment of the crude reaction mixture with an alcohol, such as ethanol, is preferably avoided, especially if there is no not wish to esterify perylene I.

The novel perylene-3,4-dicarboxylic acid imides II are preferably obtained in analogy to the above-mentioned methods by reacting the corresponding perylene-3,4-dicarboxylic acid anhydrides (known, inter alia, from Liebigs Ann. (1995) p.1229 et seq. or from Liebigs Ann./ Recueil (1997) 467 et seq.) with the amino acids IV. The reaction conditions and ratios of the educts also correspond to the above conditions.

Accordingly, another embodiment of this invention relates to a process for the preparation of perylene-3,4-dicarboxylic acid imides II, which comprises reacting a perylene-3,4-dicarboxylic acid anhydride with an amine at elevated temperature, the amine used being the amino acid IV, and the perylene-3,4-dicarboxylic acid anhydride used being the compound of the general formula V

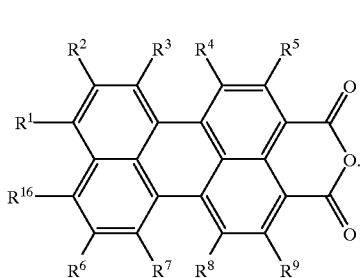

Preferred perylene-3,4-dicarboxylic acid imides II are those, wherein $R^1$ to $R^{16}$ are the groups defined above as preferred.

Particularly preferred perylene-3,4-dicarboxylic acid imides II are those, wherein $R^1$ to $R^9$ and $R^{16}$ are hydrogen, and X is a $C_1$–$C_{37}$alkanediyl radical. 11-[(N-perylene-3,4-dicarboximide)-yl]-undecanoic acid may be mentioned as example.

Another embodiment of this invention relates to perylene imide carboxylic acid derivatives VI and VII

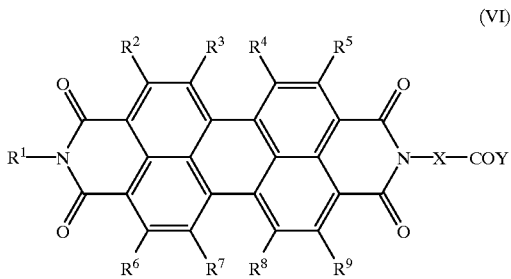

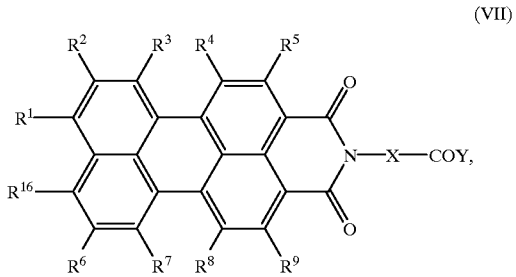

wherein $R^1$ to $R^9$ and X have the definitions given above, X not being a divalent carbocyclic or heterocyclic aromatic radical, and Y being a radical of an alcohol, of —$OR^{10}$, of an amine, of —$NR^{11}R^{12}$ or of a halogen, such as chloro or bromo.

Particularly preferred perylene imide carboxylic acid derivatives VI and VII are those, wherein $R^1$ to $R^9$ and $R^{16}$ are hydrogen, X is a $C_1$–$C_{37}$alkanediyl radical, and $R^{10}$, $R^{11}$ and $R^{12}$ are hydrogen.

The novel perylene imide carboxylic acid derivatives VI and VII are usually obtained by methods known per se (see, for example, Organikum, p.440 et seq, chap. 7.1.5.1, $9^{th}$ edition, 1969) for the preparation of carboxylates and carboxylic acid amides, so that further details may be dispensed with here. The novel perylene imide monocarboxylic acids I and the perylene-3,4-dicarboxylic acid imides II may thus by esterified by acid catalysis. Suitable catalysts are the standard known catalysts such as sulfuric acid, hydrogen chloride, toluenesulfonic acid, naphthalenesulfonic acid or hydrogen-charged acid ion exchangers.

Reactions of this kind, i.e. the esterification or formation of carboxylic acid amides, are generally interesting e.g. for the use of the novel perylenecarboxylic acids I or II as fluorescent markers.

The novel perylene imide carboxylic acids I or II are suitable, inter alia, preferably for modifying inorganic substrates such as aluminium oxide, silicium dioxide, titanium dioxide, tin oxide or silicates or clay minerals since the free carboxyl function is able to ensure adhesion to the surface.

Another embodiment of this invention relates to the use of the novel perylenes I, II, VI and VII or of their metal ion complexes as colourants, preferably as pigments and dyes, in general by methods known per se, preferably (a) for mass colouring polymers, where the polymers can be polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene or polyisoprene, or the copolymers of the cited monomers;

(b) as vat dyes or mordant dyes, for example for dyeing natural substances and, in particular, paper, wood, straw, leather, hides or natural fibre materials, such as cotton, wool, silk, jute, sisal, hemp, flax or animal hair (e.g. horsehair) and the conversion products thereof, such as viscose fibre, nitrate silk or cuprammonium rayon (rayon), preferred salts for mordanting being aluminium salts, chromium salts and iron salts;

(c) for the preparation of paints, paint systems, in particular automotive lacquers, coating compositions, paper colours, printing colours, inks, in particular for use in ink-jet printers, preferably in homogeneous solution as a fluorescent ink, and for painting and writing purposes, as well as in electrophotography, e.g. for dry copier systems (Xerox process) and laser printers;

(d) for security marking purposes, such as for cheques, cheque cards, currency notes, coupons, documents, identity papers and the like, where a special unmistakable colour impression is to be achieved;

(e) as an additive to colourants, such as pigments and dyes, where a specific colour shade is to be achieved, particularly luminous shades being preferred;

(f) for marking objects for machine recognition of these objects via the fluorescence, preferably for machine recognition of objects for sorting, e.g. including the recycling of plastics, alphanumerical prints or barcodes being preferably used;

(g) for converting the frequency of light, e.g. for turning short-wave light into long-wave visible light or for doubling or tripling the frequency of laser light in non-linear optics;

(h) for the production of passive display elements for a multitude of display, notice and marking purposes, e.g. passive display elements, notices and traffic signs, such as traffic lights;

(i) as starting material for supraconducting organic materials (via π-π-interaction, the addition of e.g. iodine usually resulting in a intermediary charge delocalisation);

(j) for marking with fluorescence in the solid state;

(k) for decorative and artistic purposes;

(l) for tracer purposes, e.g. in biochemistry, medicine, technology and natural science, where the novel colourants can be linked covalently to the substrates or via secondary valences, such as hydrogen bonds or hydrophobic interactions (adsorption);

(m) as fluorescent dyes in highly sensitive detection processes (see Z. Analyt. Chem. 1985, 320, 361), in particular as fluorescent dyes in scintillators;

(n) as dyes or fluorescent dyes in optical light collection systems, in fluorescence solar collectors (see Nachr. Chem. Tech. Lab. 1980, 28, 716), in fluorescence-activated displays (see Elektronik 1977, 26, 6), in cold light sources used for light-induced polymerisation for the preparation of plastics, for testing of materials, for example in the production of semiconductor circuits, for analysing microstructures of integrated semiconductor components, in photoconductors, in photographic processes, in display, illumination or image converter systems, where excitation is effected by electrons, ions or UV radiation, e.g. in fluorescent displays, Braun tubes or in fluorescent lamps, as part of an integrated semiconductor circuit containing dyes as such or in combination with other semiconductors, for example in the form of an epitaxy, in chemiluminescence systems, e.g. in chemiluminescent flashlights, in luminescene immunoassays or other luminescence detection processes, as signal paints, preferably for visually emphasising strokes of writing and drawings or other graphic products, for marking signs and other objects for which a particular visual colour impression is to be achieved, in dye lasers, preferably as fluorescent dyes for generating laser beams, as optical recording medium and also as Q-switches;

(o) as rheology improvers, and (p) for modifying inorganic substrates such as aluminium oxide, silicium oxide, titanium dioxide, tin oxide, magnesium oxide (especially "stone wood"), silicates, clay minerals, calcium-, gypsum- or cement-containing surfaces, for example coatings or plaster surfaces, where the free carboxyl function ensures special surface adhesion.

EXAMPLES

Example 1

4-[N-(1-hexylheptyl)-N'-perylene-3,4:9,10-bis (dicarboximide)-yl]-benzoic acid 400 mg (0.70 mmol) of N-(1-hexylheptyl)perylene-3,4:9,10-tetracarboxylic acid-3,4-anhydride-9,10-imide, 290 mg (2.10 mmol) of 4-aminobenzoic acid, 100 mg (0.46 mmol) of zinc acetate dihydrate and 4 g of imidazole are reacted for 2 h at an oil bath temperature of 130° C. The reaction mixture is taken up in 200 ml of chloroform and extracted twice with 200 ml each of 2 N hydrochloric acid. The chloroform phase is then filtered over aluminium oxide (column 20·4 cm/chloroform/glacial acetic acid (10+1)). The crude product is worked up by chromatography over silica gel/chloroform/glacial acetic acid (10+1). For further purification, the colourant is suspended in ethyl acetate and applied to a chromatographic column (silica gel/ethyl acetate), including the substrates. In this manner it is possible to separate a nonuniform forerun, the product remaining partly undissolved at the starting point. Once the forerun is nearly colourless, the mobile phase is changed (chloroform/glacial acetic acid (10+1)). The product then dissolves completely and starts to move on the column as a wide band. The combined phases of the main run, which are thin-layer chromatographically uniform, are freed from the eluant mixture and taken up in a small amount of chloroform and filtered through a D4 frit. The filtrate is transferred to a round-bottom flask, covered with a large amount of distilled water, and the chloroform is then drawn off. The precipitated colourant is separated via a frit and dried at 100° C. The precipitate stores the water especially. The product is therefore transferred to an agate mortar and the colourant is carefully ground, upon which the water bound in the precipitate is released. The precipitate is then dried and the procedure is repeated until the pure product can be powdered and dried for 24 h at 80° C. in an oil pump vacuum. Yield: 290 mg (60%), m.p.>350° C.–$R_f$ (silica gel/CHCl$_3$/ethanol/(10+1))=0.48. –$R_f$ (silca gel/CHCl$_3$/glacial acetic acid/(10+1))=0.71.–IR (KBr): n=2955 cm$^{-1}$ (m), 2926 (m), 2856 (m), 1709 (s sh), 1702 (s sh), 1698 (s), 1658 (s br.), 1618 (w), 1594 (s), 1579 (m), 1509 (w), 1460 (w), 1434 (w), 1405 (m), 1343 (s), 1254 (m), 1199 (m), 1176 (m), 1122 (w), 1108 (w), 1020 (w), 968 (w), 852 (m), 811 (s), 801 (w), 796 (w), 767 (m), 745 (m). UV (CHCl$_3$): $I_{max}$ (e)=527 nm (91000), 490 (54700), 460 (19800)–Fluorescence (CHCl$_3$): $I_{max}$=534 nm, 575.–Fluorescence in the solid state: $I_{max}$=641 nm. $C_{44}H_{40}N_2O_6$ (692.8): calcd. C 76.28, H 5.82, N 4.04; found C 76.52, H 5.60, N 4.06.

Example 2

3-[N-(1-nonyldecyl)-N'-perylene-3,4:9,10-bis(dicarboximide)-yl]-benzoic acid 300 mg (0.47 mmol) of N-(1-nonyldecyl)-perylene-3,4:9,10-tetracarboxylic acid-3,4-anhydride-9,10-imide, 190 mg (1.39 mmol) of 3-aminobenzoic acid and 4 g of imidazole are reacted without addition of zinc acetate dihydrate in analogy to Example 1 and are worked up. Yield: 160 mg (45%), m.p.>350° C.–$R_f$(silica gel/CHCl$_3$/ethanol/(10+1))= 0.50.–$R_f$ (silica gel/CHCl$_3$/glacial acetic acid/(10+1))= 0.75.–IR (KBr): n=2952 cm$^{-1}$ (m), 2925 (s), 2854(m), 1710 (s sh), 1699 (s), 1661 (s br.), 1594(s), 1579(m), 1506(w), 1449 (m br.), 1435 (m), 1405 (m), 1365 (m sh), 1355 (m sh), 1343 (s), 1303 (w), 1255 (m), 1198 (m), 1177 (m), 1149 (w), 1126 (w), 965 (w), 855 (w), 811 (s), 799 (w), 746 (m), 651 (m), 638 (w). UV (CHCl$_3$): $I_{max}$ (e)=527 nm (84200), 490 (50500), 459 (18300).–Fluorescence (CHCl$_3$): $I_{max}$=533 nm, 574. $C_{50}H_{52}N_2O_6$ (777.0): calcd. C 77.29, H 6.74, N 3.60; found C 77.47, H 6.90, N 3.61.

Example 3

2-[N-(1-nonyldecyl)-N'-perylene-3,4:9,10-bis(dicarboximide)-yl]-benzoic acid 300 mg (0.47 mmol) of N-(1-nonyldecyl)-perylene-3,4:9,10-tetracarboxylic acid-3,4-anhydride-9,10-imide, 200 mg (1.46 mmol) of 2-aminobenzoic acid (anthranilic acid), 80 mg (0.36 mmol) of zinc acetate dihydrate and 4 g of imidazole are reacted for 1 h at an oil bath temperature of 130° C. The reaction mixture is taken up in 200 ml of chloroform and is extracted in several portions with a total of 200 ml of 2 N hydrochloric acid. The aqueous phases are discarded. The chloroform phase is applied to a chromatographic column (aluminium oxide/chloroform), the product remaining firmly adsorbed on the aluminium oxide while at least two impurities can be eluted. The colourant can be desorbed by adding 10 vol.-% of glacial acetic acid to the eluant. For further purification, the colourant is chromatographed once more over silica gel/chloroform/glacial acetic acid (10+1). The combined phases of the main run, which are thin-layer chromatographically uniform, are freed from the eluant mixture and are taken up in a small amount of chloroform and filtered through a D4 frit. The filtrate is transferred to a round-bottom flask and covered with a large amount of distilled water, and the chloroform is then drawn off. The precipitated colourant is separated via a frit and dried at 100° C. The pure product is powdered in an agate mortar and dried for 24 h at 80° C. in an oil pump vacuum. Yield: 150 mg (42%), m.p. 328–330° C. (degrad.).–$R_f$(silica gel/CHCl$_3$/ethanol/(10+1))=0.30. IR (KBr): n=2950 cm$^{-1}$ (m), 2926 (s), 2854 (m), 1715 (s), 1699 (s), 1660 (s br.), 1594 (s), 1579 (m), 1505 (w), 1490 (w), 1456 (m), 1435 (m), 1405 (s), 1370 (m sh), 1351 (s sh), 1345 (s), 1300 (w), 1256 (m), 1202 (w), 1178 (w), 1140 (w), 1125 (w), 1075 (w), 960 (w), 851 (m), 810 (s), 794 (w), 747 (m), 648 (w), 635 w. UV (CHCl$_3$): $I_{max}$ (e)=526 nm (82000), 490 (49800), 458 (18500). -Fluoroescence (CHCl$_3$): $I_{max}$=534 nm, 574. $C_{50}H_{52}N_2O_6$ (777.0): calcd. C 77.29, H 6.74, N 3.60; found C 77.14, H 7.09, N 3.80.

Example 4

2-(N-(1-hexylheptyl)-N'-perylene-3,4:9,10-bis(dicarboximide)-yl)-ethanoic acid 110 mg (0.19 mmol) of N-(1-hexylheptyl)-perylene-3,4:9,10-tetracarboxylic acid-3,4-anhydride-9,10-imide and 180 mg (2.40 mmol) of glycine are stirred for 1 h at an oil bath temperature of 120° C. The batch is taken up in 500 ml of chloroform, extracted once with 100 ml of conc. hydrochloric acid and once with 200 ml of 2 N hydrochloric acid, and the chloroform phase is then washed with bidistilled water. The solution of the crude product is concentrated to about 30 ml and is then filtered over aluminium oxide (column 20·4 cm/chloroform/glacial acetic acid (10+1)). The analytically pure colourant is obtained after chromatographing the product twice over silica gel using chloroform/glacial acetic acid (10+1) as eluant. Yield: 70 mg (58%), m.p. 348–350° C.–$R_f$ (silica gel/CHCl$_3$/ethanol (10+1))=0.10. IR (KBr): n=2955 cm$^{-1}$ (m), 2929 (m), 2857 (m), 1735 (w br.), 1700 (s), 1660 (s), 1616 (w), 1595 (s), 1579 (m), 1507 (w), 1457 (w), 1437 (m), 1404 (m), 1378 (w), 1346 (s br.), 1304 (w), 1253 (m), 1195 (w), 1173 (m), 1129 (w), 993 (w), 855 (w), 810 (s), 749 (m), 623 (w). UV (CHCl$_3$): $I_{max}$ (e)=526 nm (79000), 490 (47300), 458 (16900). -Fluorescence (CHCl$_3$): $I_{max}$=537 nm, 575, 620. $C_{39}H_{38}N_2O_6$ (630.7): Calcd. C 74.27, H 6.07, N 4.44; found C 74.21, H 6.18, N 4.49.

Example 5

4-[N-(1-hexylheptyl)-N'-perylene-3,4:9,10-bis(dicarboximide)-yl]-butanoic acid 290 mg (0.51 mmol) of N-(1-hexylheptyl)-perylene-3,4:9,10-tetracarboxylic acid-3,4-anhydride-9,10-imide and 80 mg (0.78 mmol) of 4-aminobutyric acid are reacted for 2 h in 4 g of imidazole at an oil bath temperature of 140° C. The reaction mixture is taken up in 300 ml of chloroform, extracted with 200 ml of 2 N hydrochloric acid and the organic phase is then filtered over aluminium oxide (column 20·4 cm/chloroform/glacial acetic acid (10+1). The crude product is chromatographed twice over silica gel using chloroform/glacial acetic acid (10+1) as eluant, it being possible to separate several by-products with the forerun. The further purification of the colourant is carried out by extractive recrystallisation from chloroform. After the extraction is complete, the chloroform phase is covered with pentane and the closed flask is left standing for several days. The analytically pure product is collected by suction, pre-dried at 100° C., powdered in a mortar and is then freed from the remaining solvent in an oil pump vacuum (80° C., 24 h). Yield: 230 mg (70%), yield: 180 mg (56% after the extractive recrystallisation), m.p. 307–308° C.–$R_f$ (silica gel/CHCl$_3$/ethanol (10+1))=0.35

IR (KBr): n=2957 cm$^{-1}$ (m), 2926 (m), 2856 (m), 1730 (w br.), 1696 (s), 1658 (s), 1616 (w), 1595 (s), 1579 (m), 1506 (w), 1457 (w), 1442 (m), 1405 (m), 1342 (s br.), 1252 (m br.), 1177 (w), 1166 (w), 1128 (w), 902 (w), 855 (w), 810 (s), 746 (s). UV (CHCl$_3$): I$_{max}$ (e)=526 nm (81100), 490 (49100), 458 (17900).–Fluorescence (CHCl$_3$): I$_{max}$=537 nm, 575. C$_{41}$H$_{42}$N$_2$O$_6$ (658.8): calcd. C 74.75, H 6.43, N 4.25; found C 74.61, H 6.38, N 4.25.

Example 6
6-[N-(1-hexylheptyl)-N'-perylene-3,4:9,10-bis (dicarboximide)-yl]-hexanoic acid 400 mg (0.70 mmol) of N-(1-hexylheptyl)-perylene-3, 4:9,10-tetracarboxylic acid-3,4-anhydride-9,10-imide, 130 mg (1.00 mmol) of 6-aminocaproic acid and 5 g of imidazole are stirred for 2 h at an oil bath temperature of 130° C. The mixture is taken up in 200 ml of chloroform, extracted once with a small amount of conc. hydrochloric acid and once with 200 ml of 2 N hydrochloric acid, and the chloroform extracts are then washed with distilled water. The organic phase is filtered over aluminium oxide (column 10·4 cm) with addition of 10 vol.-% glacial acetic acid. The crude product is chromatographed over silica gel (column 50·4 cm)/chloroform/glacial acetic acid (10+1) and a non-uniform orange-red forerun can be separated. The combined phases of the main run, which are thin-layer chromatographically uniform, are freed from the eluant mixture, taken up in a small amount of chloroform and filtered through a D4 frit. The filtrate is transferred to a round-bottom flask, covered with a large amount of distilled water, and the chloroform is then carefully drawn off. The precipitated colourant is then separated via a frit and dried at 100° C. The pure product is powdered in an agate mortar and dried for 24 h at 80° C. in an oil pump vacuum. Yield: 280 mg (58%), m.p. 246–248° C.–R$_f$ (silica gel/CHCl$_3$/glacial acetic acid (10+1))=0.66. IR (KBr): n=2955 cm$^{-1}$ (m), 2928 (m), 2857 (m), 1730 (w sh), 1696 (s br.), 1658 (s), 1616 (w), 1595 (s), 1579 (m), 1506 (w), 1457 (w), 1439 (m), 1405 (s), 1385 (w), 1355 (m), 1342 (s), 1253 (m), 1217 (w), 1176 (w), 1126 (w), 905 (w), 855 (w), 810 (s), 747 (m), 668 (w). UV (CHCl$_3$): I$_{max}$ (e)=526 nm (80800), 489 (48400), 458 (17700). –Fluorescence (CHCl$_3$): I$_{max}$=535 nm, 574. C$_{43}$H$_{46}$N$_2$O$_6$ (686.9): calcd. C 75.19, H 6.75, N 4.08; found C 75.28, H 6.94, N 4.08.

Example 7
11-[N-(1-hexylheptyl)-N'-perylene-3,4:9,10-bis (dicarboximide)-yl]-undecanoic acid 300 mg (0.52 mmol) of N-(1-hexylheptyl)-perylene-3, 4:9,1 0-tetracarboxylic acid-3,4-anhydride-9,10-imide and 160 mg (0.79 mmol) of 11-aminoundecanoic acid are reacted for 1 h in 4 g of imidazole at an oil bath temperature of 130° C. The batch is then taken up in 200 ml of chloroform and extracted with 200 ml of 2 N hydrochloric acid. The organic phase is then filtered over aluminium oxide (column 20·4 cm/chloroform/glacial acetic acid (10+ 1). The purification of the colourant is carried out by chromatography over silica gel, using chloroform/glacial acetic acid (10+1) as eluant. Minor fluorescent impurities can be separated by chromatographing again over silica gel/chloroform/ethanol (10+1). In spite of the high R$_f$-vlaue on the thin-layer chromatogramme, the product moves very slowly on the second column, which is why the eluant is changed after the impurities have been washed out (chloroform/ethanol (4+1)). Yield: 210 mg (53%), m.p. 168–170° C.–R$_f$ (silica gel/CHCl$_3$/ethanol/(10+1))=0. IR (KBr): n=2953 cm$^{-1}$ (m), 2926 (s), 285 (m), 1728 (m sh), 1697 (s), 1658 (s), 1615 (w), 1595 (m), 1579 (m), 1508 (w), 1458 (m), 1439 (m), 1405 (s), 1389 (w), 1355 (m sh), 1342 (s), 1254 (m), 1217 (w), 1176 (m), 1126 (w), 1108 (w), 1092 (w), 853 (m), 810 (s), 796 (w), 746 (m), 655 (w). UV (CHCl$_3$): I$_{max}$ (e)=526 nm (82100), 490 (49400), 458 (18000).–Fluorescence (CHCl$_3$): I$_{max}$=537 nm, 575. C$_{48}$H$_{56}$N$_2$O$_6$ (757.0): calcd. C 76.16, H 7.46, N 3.70; found C 76.10, H 7.45, N 3.70.

Example 8
11-[(N-perylene-3,4-dicarboximide)-yl]-undecanoic acid 120 mg (0.37 mmol) of perylene-3,4-dicarboxylic anhydride are stirred with 110 mg (0.55 mmol) of 11-aminoundecanoic acid in 3 g of imidazole at 120° C. After one hour, the reaction mixture is taken up in 150 ml of chloroform, extracted once with 150 ml of 2 N hydrochloric acid and the aqueous phase is discarded. The organic phase is concentrated and chromatographed over aluminium oxide/chloroform/glacial acetic acid (10+1). For further purification, the product is chromatographed over silica gel/chloroform /glacial acetic acid (10+1), which gives the product in the form of a wide orange band. Any remaining fluorescent impurity is separated over silica gel/chloroform /ethanol (10+1). The combined phases of the main run, which are thin-layer chromatographically uniform, are freed from the eluant mixture and taken up in a small amount of chloroform/glacial acetic acid and filtered through a D4 frit. The filtrate is transferred to a round-bottom flask, covered with a large amount of distilled water, and the chloroform is then drawn off. The precipitated colourant is then separated via a frit and dried at 100° C. The pure product is powdered in an agate mortar and dried for 24 h at 80° C. in an oil pump vacuum. Yield: 110 mg (59%), m.p. 186–187 ° C.–R$_f$ (silica gel/CHCl$_3$/glacial acetic acid (10+1))=0.66. IR (KBr): n=3200 cm$^{-1}$ (w br.), 3050 (w), 2927 (s), 2854 (m), 1733 (m), 1700 (m sh), 1691 (s), 1651 (s), 1618 (w), 1592 (s), 1571 (m), 1500 (w), 1435 (w), 1422 (w), 1410 (w), 1383 (m), 1374 (m), 1356 (s), 1293 (m), 1246 (m), 1091 (w), 838 (w), 810 (s), 754 (m). UV (CHCl$_3$): I$_{max}$ (e)=506 nm (29900), 484 (30800).–Fluorescence (CHCl$_3$): I$_{max}$=541 nm, 574. C$_{33}$H$_{31}$NO$_4$ (505.6): calcd. C 78.39, H 6.18, N 2.77; found C 78.20, H 6.07, N 2.81.

Example 9
N-(1-hexylheptyl)-N'-(6-hexanoic acid ethyl ester)-perylene-3,4:9,10- bis(dicarboximide)

150 mg (0.22 mmol) of 6-[N-(1-hexylheptyl)-N'-perylene-3,4:9,10-bis(dicarboximide)-yl]-hexanoic acid (of Example 6), 22 mg (0.24 mmol) of glycerol and 100 mg of toluenesulfonic acid monohydrate are heated to boiling in 20 ml of chloroform with about 5% ethanol. The chloroform is distilled off continuously, fresh chloroform being added from time to time. The reaction is observed by thin-layer chromatography (silica gel/chloroform/ethanol (10+1)) using the educt as reference) and is stopped after 3.5–4 h. The main product with the highest R$_f$-value can be roughly separated from the other six by-products by column chromatography (silica gel/chloroform/ethanol (10+1)). The ultrapurification is carried out over aluminium oxide (column 40·4 cm) using chloroform as eluant, the product moving very slowly. The remaining impurities, however, remain firmly adsorbed to the column material. The pure colourant fraction is charged with methanol and filtered through a D4 frit. The solvent is removed by distillation and the product is then dried at 80° C. in an oil pump vacuum. Yield: 52 mg (33%), m.p. 192–193° C.–R$_f$ (silica gel/ CHCl$_3$/ethanol/(10+1))=0.83. IR (KBr): n=2956 cm$^{-1}$ (m), 2928 (m), 2858 (m), 1 724 (m), 1697 (s), 1658 (s), 1596 (s), 1578 (m), 1508 (w), 1458 (w), 1438 (m), 1404 (m), 1343 (s), 1253 (m), 1178 (m), 1126 (w), 1109 (w), 1084 (w), 1032 (w), 853 (w), 810 (m), 796 (w), 747 (m). UV (CHCl$_3$): I$_{max}$ (e)=526 nm (81350), 489 (48800), 458 (18000).–Fluorescence (CHCl$_3$): I$_{max}$=535 nm, 574, 618 br.–

Fluorescence in the solid state: $I_{max}$=528 nm, 570, 625
$C_{45}H_{50}N_2O_6$ (714.9): calcd. C 75.60, H 7.05, N 3.92; found C 75.35, H 6.99, N 3.94.

What is claimed is:

1. A perylene imide monocarboxylic acid of the general formula I

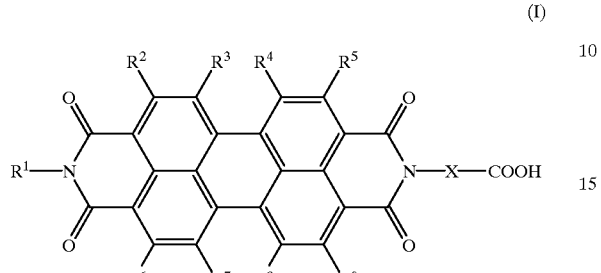

(I)

wherein $R^1$, $R^2$, $R^3$, $R^4$, $R^5$, $R^6$, $R^7$, $R^8$, $R^9$ are identical or different and are hydrogen, or one to nine radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, wherein the alkyl groups can be substituted by the following groups: fluoro, cyano, —OCOR$^{13}$, —OR$^{11}$, —OCOOR$^{13}$, —CON(R$^{11}$)(R$^{12}$) or —OCONHR$^{13}$;

—OR$^{10}$, —CN, —NR$^{11}$R$^{12}$, —COR$^{13}$, —NR$^{14}$COR$^{13}$, —NR$^{10}$COOR$^{13}$, —NR$^{10}$CONR$^{11}$R$^{12}$, —NHSO$_2$R$^{13}$, —SO$_2$R$^{13}$, —SOR$^{13}$, —SO$_2$OR$^{13}$, —CONR$^{11}$R$^{12}$, —SO$_2$NR$^{11}$R$^{12}$, —N=NR$^{15}$, —OCOR$^{13}$ and —OCONHR$^{13}$, wherein pairs of adjacent radicals can form a carbocyclic or heterocyclic ring, wherein $R^{13}$ is $C_1$–$C_{18}$alkyl, $C_6$–$C_{10}$aryl, or benzyl which is unsubstituted or substituted by halgen, $C_1$–$C_4$alkyl or $C_1$–$C_4$alkoxy, or a five- to seven-membered heterocyclic radical, $R^{11}$ and $R^{12}$ are each independently of the other hydrogen; $C_1$–$C_{18}$alkyl, $C_3$–to $C_{24}$cycloalkyl, $C_6$–$C_{10}$aryl or 5- to 7-membered heteroaryl, each of which is unsubstituted or substituted by cyano groups or hydroxy groups, or wherein $R^{11}$ and $R^{12}$, together with at least one of the other radicals $R^2$ to $R^9$, are a 5- or 6-membered carbocyclic or heterocyclic ring, $R^{10}$ is hydrogen, $C_1$–$C_{18}$alkyl, $C_3$–to $C_{24}$cycloalkyl, $C_6$–$C_{10}$aryl or 5- to 7-membered heteroaryl, $R^{14}$ is hydrogen; $C_1$–$C_{18}$alkyl, $C_3$–to $C_{24}$cycloalkyl, $C_1$–$C_4$alkylaryl, each of which is unsubstituted or substituted by cyano groups, hydroxy groups or $C_1$–$C_4$alkoxycarbonyl groups; $C_6$–$C_{10}$aryl which is unsubstituted or substituted by halogen, $C_1$–$C_4$alkyl groups or $C_1$–$C_4$alkoxy groups, or a 5- to 7-membered heterocycle, $R^{15}$ is the radical of a coupling component, or $C_6$–$C_{10}$aryl which is unsubstituted or substituted by halogen, $C_1$–$C_4$alkyl groups or $C_1$–$C_4$alkoxy groups, and X is $C_1$–$C_{37}$alkanediyl, $C_2$–$C_{37}$alkenediyl, $C_2$–$C_{37}$alkynediyl, $C_5$–$C_{12}$cycloalkylene, $C_5$–$C_{12}$cycloalkenylene, $C_5$–$C_{12}$cycloalkynylene, a divalent carbocyclic or heterocyclic aromatic radical.

2. A perylene imide carboxylic acid derivative VI

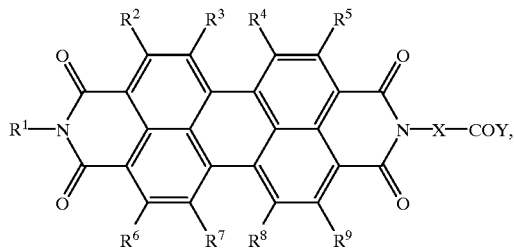

(VI)

wherein $R^1$, $R^2$, $R^3$, $R^4$, $R^5$, $R^6$, $R^7$, $R^8$, $R^9$ are identical or different and are hydrogen, or one to nine radicals are a radical selected from the group consisting of an unsubstituted or substituted carbocyclic aromatic radical, an unsubstituted or substituted heterocyclic aromatic radical, halogen, unsubstituted or substituted $C_1$–$C_{18}$alkyl, wherein the alkyl groups can be substituted by the following groups: fluoro, cyano, —OCOR$^{13}$, —OR$^{11}$, —OCOOR$^{13}$, —CON(R$^{11}$)(R$^{12}$) or —OCONHR$^{13}$;

—OR$^{10}$, —CN, —NR$^{11}$R$^{12}$, —COR$^{13}$, —NR$^{14}$COR$^{13}$, —NR$^{10}$COOR$^{13}$, —NR$^{10}$CONR$^{11}$R$^{12}$, —NHSO$_2$R$^{13}$, —SO$_2$R$^{13}$, —SOR$^{13}$, —SO$_2$OR$^{13}$, —CONR$^{11}$R$^{12}$, —SO$_2$NR$^{11}$R$^{12}$, —N=NR$^{15}$, —OCOR$^{13}$ and —OCONHR$^{13}$, wherein pairs of adjacent radicals can form a carbocyclic or heterocyclic ring, wherein $R^{13}$ is $C_1$–$C_{18}$alkyl, $C_6$–$C_{10}$aryl, or benzyl which is unsubstituted or substituted by halgen, $C_1$–$C_4$alkyl or $C_1$–$C_4$alkoxy, or a five- to seven-membered heterocyclic radical, $R^{11}$ and $R^{12}$ are each independently of the other hydrogen; $C_1$–$C_{18}$alkyl, $C_3$–to $C_{24}$cycloalkyl, $C_6$–$C_{10}$aryl or 5- to 7-membered heteroaryl, each of which is unsubstituted or substituted by cyano groups or hydroxy groups, or wherein $R^{11}$ and $R^{12}$, together with at least one of the other radicals $R^2$ to $R^9$, are a 5- or 6-membered carbocyclic or heterocyclic ring, $R^{10}$ is hydrogen, $C_1$–$C_{18}$alkyl, $C_3$–to $C_{24}$cycloalkyl, $C_6$–$C_{10}$aryl or 5- to 7-membered heteroaryl, $R^{14}$ is hydrogen; $C_1$–$C_{18}$alkyl, $C_3$–to $C_{24}$cycloalkyl, $C_1$–$C_4$alkylaryl, each of which is unsubstituted or substituted by cyano groups, hydroxy groups or $C_1$–$C_4$alkoxycarbonyl groups; $C_6$–$C_{10}$aryl which is unsubstituted or substituted by halogen, $C_1$–$C_4$alkyl groups or $C_1$–$C_4$alkoxy groups, or a 5- to 7-membered heterocycle, $R^{15}$ is the radical of a coupling component, or $C_6$–$C_{10}$aryl which is unsubstituted or substituted by halogen, $C_1$–$C_4$alkyl groups or $C_1$–$C_4$alkoxy groups, and X is $C_1$–$C_{37}$alkanediyl, $C_2$–$C_{37}$alkenediyl, $C_2$–$C_{37}$alkynediyl, $C_5$–$C_{12}$cycloalkylene, $C_5$–$C_{12}$cycloalkenylene, $C_5$–$C_{12}$cycloalkynylene, a divalent carbocyclic or heterocyclic aromatic radical, and Y is a radical of an alcohol, of —OR$^{10}$, of an amine, of —NR$^{11}$R$^{12}$ or of a halogen.

3. A process for the preparation of perylene imide monocarboxylic acid according to claim 1, which comprises reacting a perylene imide anhydride with a primary amine at elevated temperature, the perylene anhydride imide III

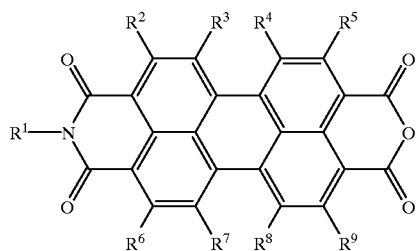
(III)
being reacted with an amino acid of formula IV
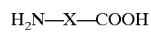    IV.
* * * * *